United States Patent
Okada (10) Patent No.: US 6,636,632 B2
(45) Date of Patent: Oct. 21, 2003

(54) IMAGE PROCESSOR AND IMAGE PROCESSING METHOD

(75) Inventor: Masahiro Okada, Ogaki (JP)

(73) Assignee: Ibiden Co., Ltd., Ogaki (JP)

( * ) Notice: Subject to any disclaimer, the term of this patent is extended or adjusted under 35 U.S.C. 154(b) by 0 days.

(21) Appl. No.: 09/772,927

(22) Filed: Jan. 31, 2001

(65) Prior Publication Data

US 2001/0053242 A1 Dec. 20, 2001

Related U.S. Application Data

(63) Continuation of application No. PCT/JP99/04096, filed on Jul. 29, 1999.

(30) Foreign Application Priority Data

Jul. 31, 1998 (JP) .............................................. 10-216772

(51) Int. Cl.$^7$ ................................................ G06K 9/46
(52) U.S. Cl. .................................... 382/194; 356/239.3
(58) Field of Search ................................. 382/100, 154, 382/135, 144, 218, 175, 193, 194, 147, 148, 192, 195, 197, 145, 209, 149, 256, 257, 258; 356/237.2, 239.3, 394

(56) References Cited

U.S. PATENT DOCUMENTS

| | | | | |
|---|---|---|---|---|
| 4,578,810 A | * | 3/1986 | MacFarlane et al. | ........ 382/135 |
| 4,830,497 A | * | 5/1989 | Iwata et al. | .................. 356/394 |
| 5,111,411 A | * | 5/1992 | Browne | ....................... 364/559 |
| 5,608,816 A | * | 3/1997 | Kawahara et al. | .......... 382/149 |

* cited by examiner

Primary Examiner—Jayanti K. Patel
Assistant Examiner—Seyed Azarian
(74) Attorney, Agent, or Firm—Oblon, Spivak, McClelland, Maier & Neustadt, P.C.

(57) ABSTRACT

An image processor wherein, with respect to pixels included in a pattern image and in a plural directions from a selected pixel among pixels, a number of same kind of pixels which consecutively continues from the selected pixel is counted. A processing recognition area effective signal that shows a range in which an area to be processed exists is produced. Whether the selected pixel is a processing candidate pixel is determined based on a determination whether the number is larger, in the plural directions, than a reference value. A processing image is made by comparing the processing candidate pixel and the processing recognition area effective signal.

19 Claims, 9 Drawing Sheets

IMAGE PROCESSOR AND IMAGE PROCESSING METHOD

CROSS-REFERENCE TO RELATED APPLICATION

The present application claims priority under 35 U.S.C. §119 to Japanese Patent Application No.10-216772, filed Jul. 31, 1998. Further, the present application is a continuation under 35 U.S.C. §120 to International Application No. PCT/JP99/04096, filed Jul. 29, 1999, entitled "IMAGE PROCESSOR." The contents of these applications are incorporated herein by reference in their entirety.

BACKGROUND OF THE INVENTION

1. Field of the Invention

The present invention relates to an image processor and image processing method.

2. Discussion of the Background

An inspected object such as a printed wiring board often includes a shape that often misjudged as a defect by a wiring pattern inspecting apparatus. Because of this a part containing the shape must not be a target of the inspection. A part of a hole connecting between layers, such as a through hole and a photo via hole (hereinafter referred to as "a via hole") is correspondent to the shape. For example, Japanese Patent Laid-Open No. 6-294626 bulletin disclosed a conventional wiring pattern inspecting apparatus comprising a quality inspection of a wiring pattern by extracting a true defect data based on a pattern image got by capturing an inspected object, and a hole mask image made separately. That is, among defect candidate data in the pattern image, a data not correspond with the hole mask image is a true defect data. This hole mask image is made by contrasting a hole measurement signal showing a part comprising a shape considered to be a through hole in a pattern image and a hole recognition effective signal provided from a specification of the inspected object. The contents of Japanese Patent Laid-Open No. 6-294626 are incorporated herein by reference in their entirety.

Figure 11:
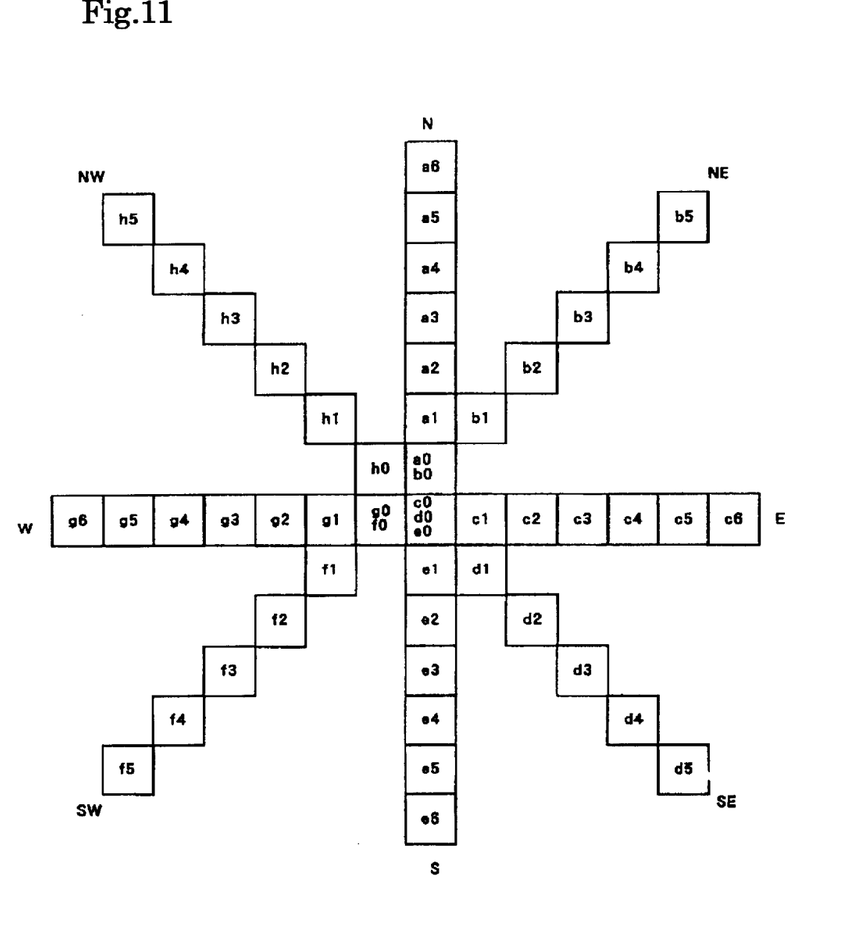
FIG. 11 is an explanatory drawing of a counting method of a pixel on each direction according to a conventional wiring pattern inspecting apparatus.

In this conventional technique, the extraction of the hole measurement signal from the pattern image is done as follows. As shown in FIG. 11, a number that a black pixel continues is counted on every eight directions of N, NE, E, SE, S, SW, W, NW from a point where four black pixels are gathered in a binarized pattern image. And the hole measurement signal is turned on about each pixel of the point if there is a number that the black pixel continues in a predetermined range (an upper limit value and a lower limit value of a number of pixel corresponding to a through hole radius) about each direction.

Figure 3:
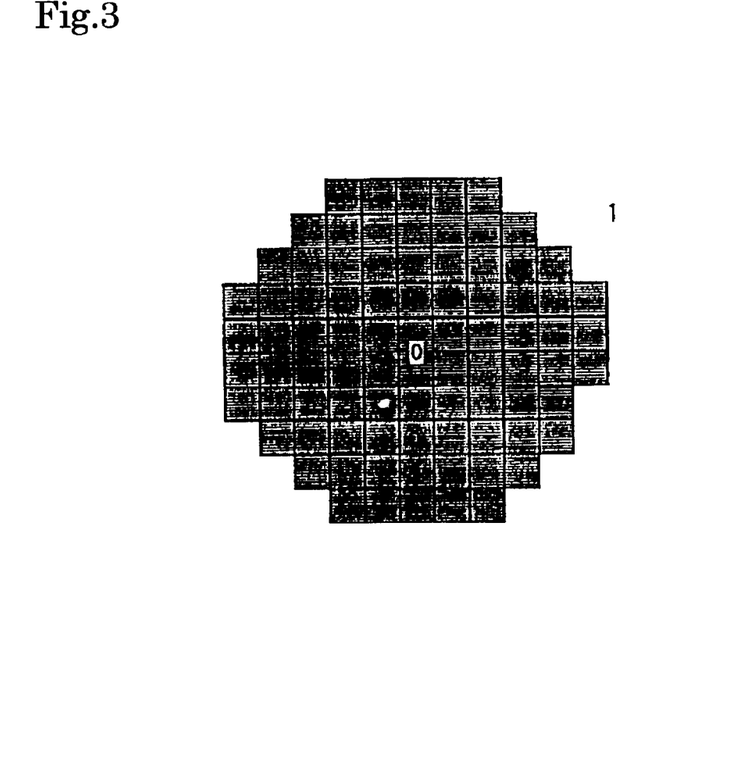
FIG. 3 is an explanatory drawing of a binary image of a through hole.

However, the conventional wiring pattern inspecting apparatus includes a problem explained in the following. A penetration hole such as a through hole can be coped with, but a non-through hole such as a blind via hole formed by a laser process or a photo via hole cannot. The cause is included in a difference on a binarized pattern image with a through hole and a photo via hole. A through hole is a penetration hole, and then if an internal pixel of the through hole is binarized, the pixel becomes black by all means. Because of this, on a binarized pattern image, the through hole appears as an approximately circular mass of black pixels as shown in FIG. 3. Therefore the through hole can be recognized by a measurement such as FIG. 11. Still, in FIG. 3, "0" shows a black level with a white level "1"(the same in FIG. 4, FIG. 13 and so forth).

Figure 4:
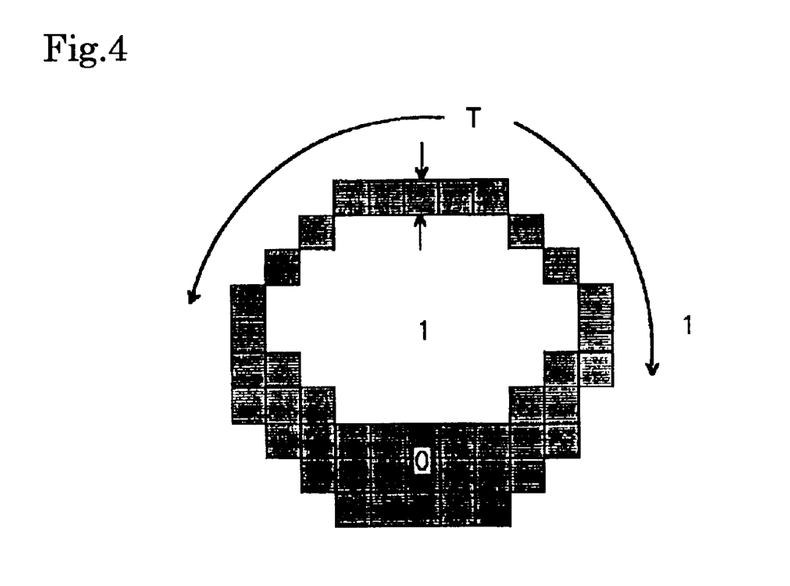
FIG. 4 is an explanatory drawing of a binary image of a photo via hole.
Figure 12:
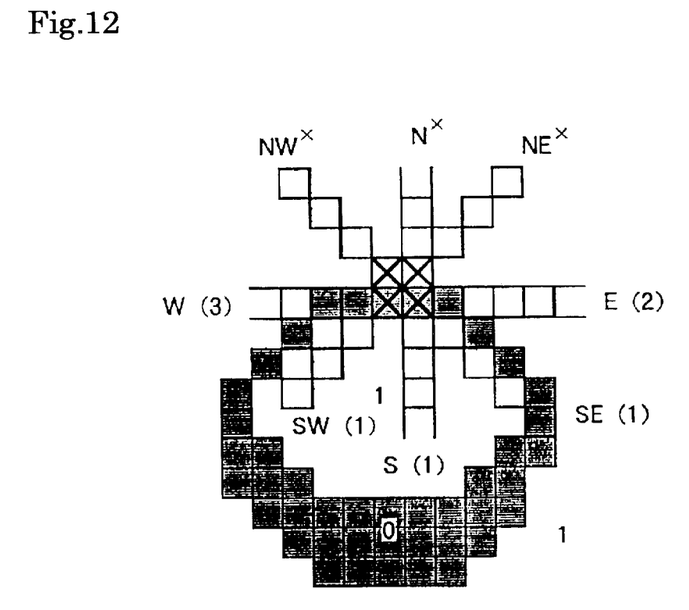
FIG. 12 is an explanatory drawing of a measurement of a photo via hole according to the conventional wiring pattern inspecting apparatus.

On the contrary, as for a photo via hole and so on, an internal pixel does not always become black because base copper in the hole shines dully. So, as shown in FIG. 4, on a binarized pattern image, the photo via hole is recognized as a black pixel area of a distorted shape. There can be a part T that has only one pixel width in the black pixel area. If the measurement such as FIG. 11 is done with the part T, as shown in FIG. 12, a count start pixel on a certain direction (N, NE, NW) does not become black. Then, a hole measurement signal cannot be turned on about this part T. Therefore, the measurement such as FIG. 11 cannot be done on this part T. Still, in FIG. 12, sign "x" referred right of a direction sign shows that the count on the direction cannot be done. And, a number in parentheses on right of a direction sign shows a count number on the direction (the same in FIG. 13).

Figure 1:
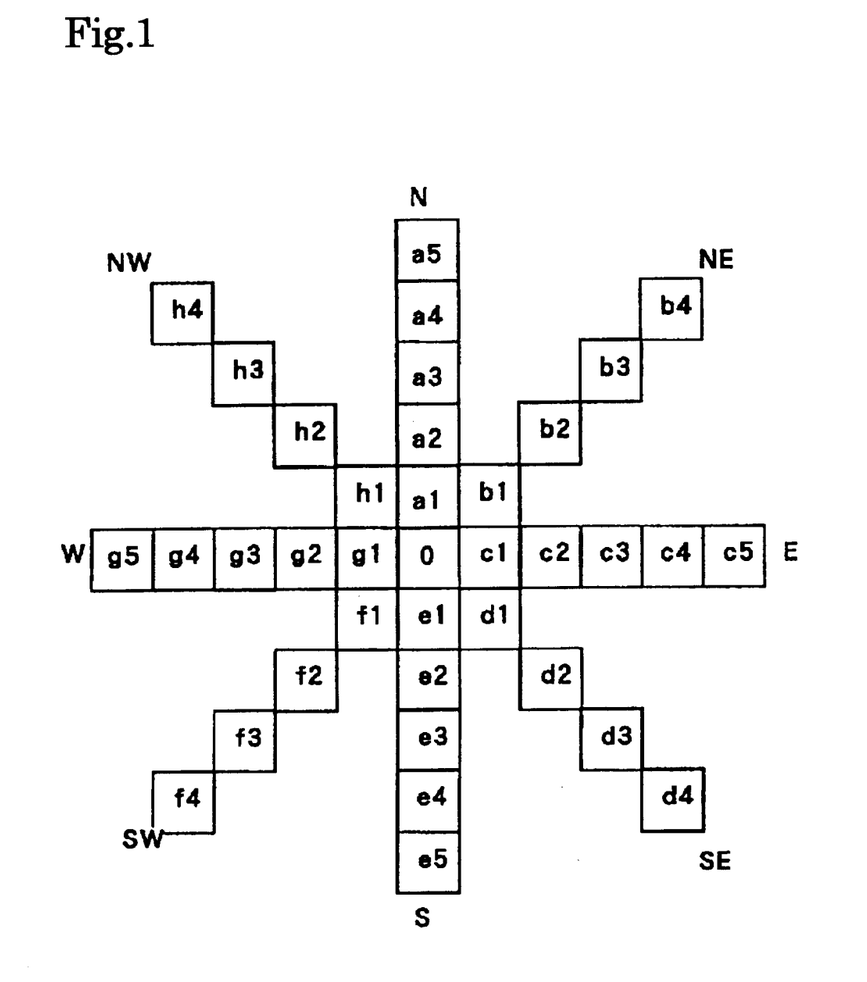
FIG. 1 is an explanatory drawing of a counting method of a pixel on each direction according to a wiring pattern inspecting apparatus of the present invention.

Although, by paying attention to an area except for the part T in a shape shown in FIG. 4, the measurement such as FIG. 1 looks possible, the number is not in the predetermined range. A case that the measurement such as FIG. 11 is really possible is extremely limited. Therefore, by a hole mask image of the conventional technique, the coat-ability of a photo via hole is bad, because an appropriate hole mask image can not be made. As a result in a case of an inspection of a wiring pattern, a lot of false signal occurs, and then the inspecting apparatus is inconvenience.

Figure 13:
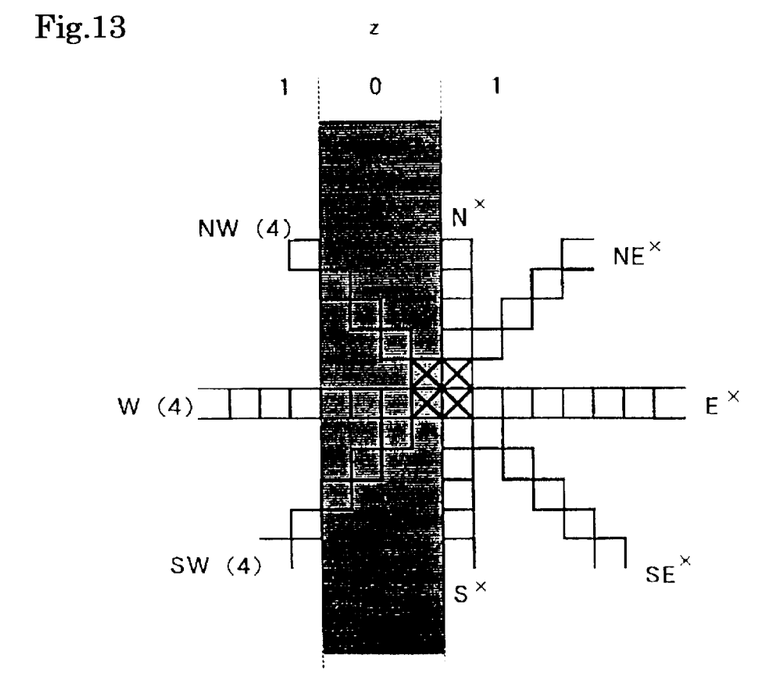
FIG. 13 is an explanatory drawing of a measurement of a conductor spacing insulation part according to the conventional wiring pattern inspecting apparatus.

By the way, in FIG. 12, a value of a numerical sum of a black pixel on each direction becomes, even the part T in FIG. 4, a positive finite value (3+1+1+1+2=8). Therefore, by setting a constant upper limit value in the value of the sum, the measurement such as FIG. 11 can recognize the part T. However, when the measurement is done with a parallel pattern consisting of a conductor spacing Z of width in unison with a diameter of a photo via hole as shown in FIG. 13, the value of the sum (4+4+4=12) can become equal to or less than the upper limit value. This means a place that is not a photo via hole is recognized a place that is a photo via hole. If there is a hole recognition effective signal near the parallel pattern, an unnecessary hole mask is generated, and then the reliability of the inspection is dropped. Although, it is conceivable that the affine transformation (a parallel transfer, magnification revision, a turn transfer) is made on the pattern image for matching, the inspection tact time increases largely.

SUMMARY OF THE INVENTION

According to one aspect of the invention, an image processor includes a pattern image making unit, a judgment unit, a recognition area making unit, a processing candidate authorization unit and a processing image making unit. The pattern image making unit is for making a pattern image formed from pixel data obtained by capturing a pattern of an object. The judgment means is for counting, with respect to pixels included in the pattern image and in a plural directions from a selected pixel among the pixels, a number of same kind of pixels which consecutively continues from the selected pixel, and for determining in the plural directions whether the number is larger than a reference value. The recognition area making unit is for producing a processing recognition area effective signal that shows a range in which an area to be processed exists with respect to the object. The processing candidate authorization unit is for determining whether the selected pixel is a processing candidate pixel based on a determination of the judgment unit. The processing image making unit is for making processing image by comparing the processing candidate pixel and the processing recognition area effective signal.

According to another aspect of the invention, an image processor includes a pattern image making unit, a diameter judging unit, a mask recognition area making unit, a candidate authorization unit, a mask making unit and an inspecting unit. The pattern image making unit is for making a pattern image formed from pixel data obtained by capturing a wiring pattern of an object to be inspected. The diameter judging unit is for counting, with respect to pixels included in the pattern image and in a plural directions from a selected pixel among the pixels, a number of same kind of pixels which consecutively continues from the selected pixel, and for determining in the plural directions whether the number is larger than a reference value. The mask recognition area making unit is for producing a mask recognition effective signal that shows a range in which an area which is outside an inspection area exists with respect to the object. The mask candidate authorization unit is for determining whether the selected pixel is a mask candidate pixel based on a determination of the diameter judging unit. The mask making unit is for making a mask image by comparing the mask candidate pixel and the a mask recognition effective signal. The inspecting unit is for extracting a defect shape from a part of the pattern image except for the mask image.

According to yet another aspect of the invention, an image processing method includes making a pattern image formed from pixel data obtained by capturing a pattern of an object. With respect to pixels included in the pattern image and in a plural directions from a selected pixel among the pixels, a number of same kind of pixels which consecutively continues from the selected pixel is counted. In the plural directions, whether the number is larger than a reference value is determined. A processing recognition area effective signal that shows a range in which an area to be processed exists with respect to said object is produced. Whether the selected pixel is a processing candidate pixel is determined based on a determination whether the number is larger than a reference value. A processing image is made by comparing the processing candidate pixel and the processing recognition area effective signal.

At first, the wiring pattern inspecting apparatus captures a wiring pattern of an inspected object, and makes a pattern image consisting of pixel data got by capturing the wiring pattern. In the case the pixel data are binarized, each pixel in the pattern image is either of a black pixel or a white pixel. Generally, a pixel on a wiring pattern is a white pixel, and a pixel between patterns is a black pixel. And every pixel in a via hole is a black pixel ideally. However, a black pixel group in the via hole can be distorted really, because one part becomes a white pixel for variations of luminosity values before the binarization. Operations until this step is done by a pattern image making means.

Next, about each pixel in the pattern image, a diameter judgment is done by a diameter judging means. The diameter judgment is done as follows. The number that a black pixel continues is counted from a selected one pixel as a starting point on each direction of a plural number (4, 8, 12, 16 directions and so forth). That is, a measurement start pixel of an each direction is one point of a pixel as shown in FIG. 1. At this point the present invention differs from the conventional technique that a measurement start pixel is not always one point such as FIG. 11. Therefore, the counted number becomes 0 or a natural number. And then, the selected pixel is judged as following. When the counted number is a natural number of less than or equal to a predetermined value (an upper limit value), the direction is judged to be good. On the contrary, when the counted number is 0 or greater than the predetermined value, the direction is judged to be no-good. These processes are the diameter judgment, and done about each pixel in the pattern image.

Still, the upper limit value is a value corresponding to a size of an inspection outside area such as a via hole, but the value may not be the same about all directions. The reason is because the upper limit value may be different in a direction corresponding with X direction or Y direction and another diagonal direction in the pattern image. And the reason is because a shape in itself of the inspection outside area may not be always circular. In addition, the counting on each direction may be stopped at a point when the counted number exceeds the upper limit value. So, the counting is not necessary to be continued till a point where a continuation of a black pixel breaks off.

In this wiring pattern inspecting apparatus, a mask recognition area making means makes a mask recognition effective signal in parallel with a work of the diameter judgment. The mask recognition effective signal shows a range that there can be an inspecting outside area in an inspected object. The making processes are as follows. A standard position where there is an inspecting outside area such as a via hole in an inspected object has been input into the wiring pattern inspecting apparatus separately. The standard position may be input from a design data of the inspected object, or may be input from a measurement result of a measurement standard board that is only formed such as a via hole. On a real inspected object, the mask recognition effective signal is usually made by expanding to a moderate width because a position of an inspecting outside area slips a little off from the standard position by reason of a dispersion of an individual. A coefficient of the expanding time is determined by such as a precision described for the inspected object.

A result of the diameter judgment is sent to a mask candidate authorization means, and then authorized the selected pixel to a mask candidate pixel or not. Preferably this authorization is done as follows. A number of a direction that the judgment result is good is counted. Then, the number of a direction is compared with a predetermined threshold, and then if the number is more than or equal to the threshold, the selected pixel is authorized to a mask candidate pixel. When the threshold is a total number of the direction, the selected pixel authorized as a mask candidate pixel is a pixel in an area where a black pixel exists only in a diameter corresponding to the upper limit value. A black pixel in a via hole is the example. A pixel on a wiring pattern does not become a mask candidate pixel because the pixel is white. In addition, usually, a pixel between patterns does not become a mask candidate pixel because the pixel continues for long distance and so does not fit in a diameter corresponding to the upper limit value, even if the pixel is black. At this point, a defect based on a pinhole becomes a mask candidate pixel, but the defect is removed later.

The work described above is done about every black pixel in the pattern image. By the work, a mask candidate pixel is become, among black pixels, by a pixel in an inspecting outside area such as a via hole and by a pixel to be caused by a defect such as a pinhole.

In usual case, a predetermined threshold compared with a number of a direction is the same as a total number of the direction (4, 8, 12, 16 directions and so forth). The reason is as follows. The number that a black pixel continues should be within the upper limit value because an inspecting outside area such as a via hole is surrounded by a land of a wiring pattern usually. Therefore, even if the number is counted into any direction, the counting faces with a white pixel of a land by all means. If a black pixel continues for a long distance that exceeds the upper limit value on a certain direction, usual it is not a via hole and so on but a part between patterns.

But, this may not be always so. By a precision prescribed for an inspected object, there is a case that to some extent broken out in a land of a circumference of a via hole is permitted. In that case, the number that a black pixel continues on a direction going through the broken out part may be greater than the upper limit value. To authorize this selected pixel to a mask candidate pixel, the threshold must be turned into a few values than the total number of a direction. To be able to cope in case of both, it is preferable the threshold is made to be varying and includes the total number of a direction in the variable range.

However, the broken out part is usually only one place in a circumference of one via hole, and a remainder of the land should continue. Because a broken out of a land is occurs for an adjustment accuracy of a center position with a via hole and a land. Therefore, if the threshold turned into a few values than the total number of a direction, it is preferable to authorize a selected pixel to a mask candidate pixel only in a case that a number that a direction of that counted number is less than or equal to the upper limit value continues is equal to or more than the threshold value.

After the mask candidate pixel and the mask recognition effective signal is prepared, a mask making means compares them, and then makes a mask image. That is, the mask image is made of an extracted pixel that is a mask candidate pixel corresponding with the mask recognition effective signal. By this, a pixel in an inspection outside area such as a via hole among mask candidate pixels is removed besides . A pixel to be caused by a defect of a pinhole and so on is cut off here, so the pixel is not masked. When a mask candidate pixel corresponding with a mask recognition effective signal is extracted, a mask image can be made of only the pixel itself or can be made of pixels multiplied the pixel by some magnification. In this way, all black pixels in a binarized pattern image are just covered by the mask image.

After the mask image is made, an inspecting means does a last inspection. The inspecting means extracts a defect shape from a part except a part of the mask image among the pattern image. In a part of the mask image, even if a defect shape is inspected, it is ignored because it is caused by a via hole. At this point, the mask image made by the mask making means is just size, so reliability of an inspection in a vicinity of an inspecting outside area such as a via hole is not lost, and besides, the occurrence of a false signal is prevented.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DESCRIPTION OF THE PREFERRED EMBODIMENTS

The preferred embodiments will now be described with reference to the accompanying drawings, wherein like reference numerals designate corresponding or identical elements throughout the various drawings.

A wiring pattern inspecting apparatus according to this embodiment inspects a quality of a wiring pattern formed on a printed wiring board. This wiring pattern inspecting apparatus has, as shown in a block diagram of FIG. 2, an imaging system 2 and an inspecting unit 31 and a mask processing unit 4 of the meantime. And, furthermore, a master CPU 32 to do total general control and a terminal 33 for indication of operation by an operator and a test result are comprised. A communication bus 53 connects the inspection unit 31 and the master CPU 32.

Figure 2:
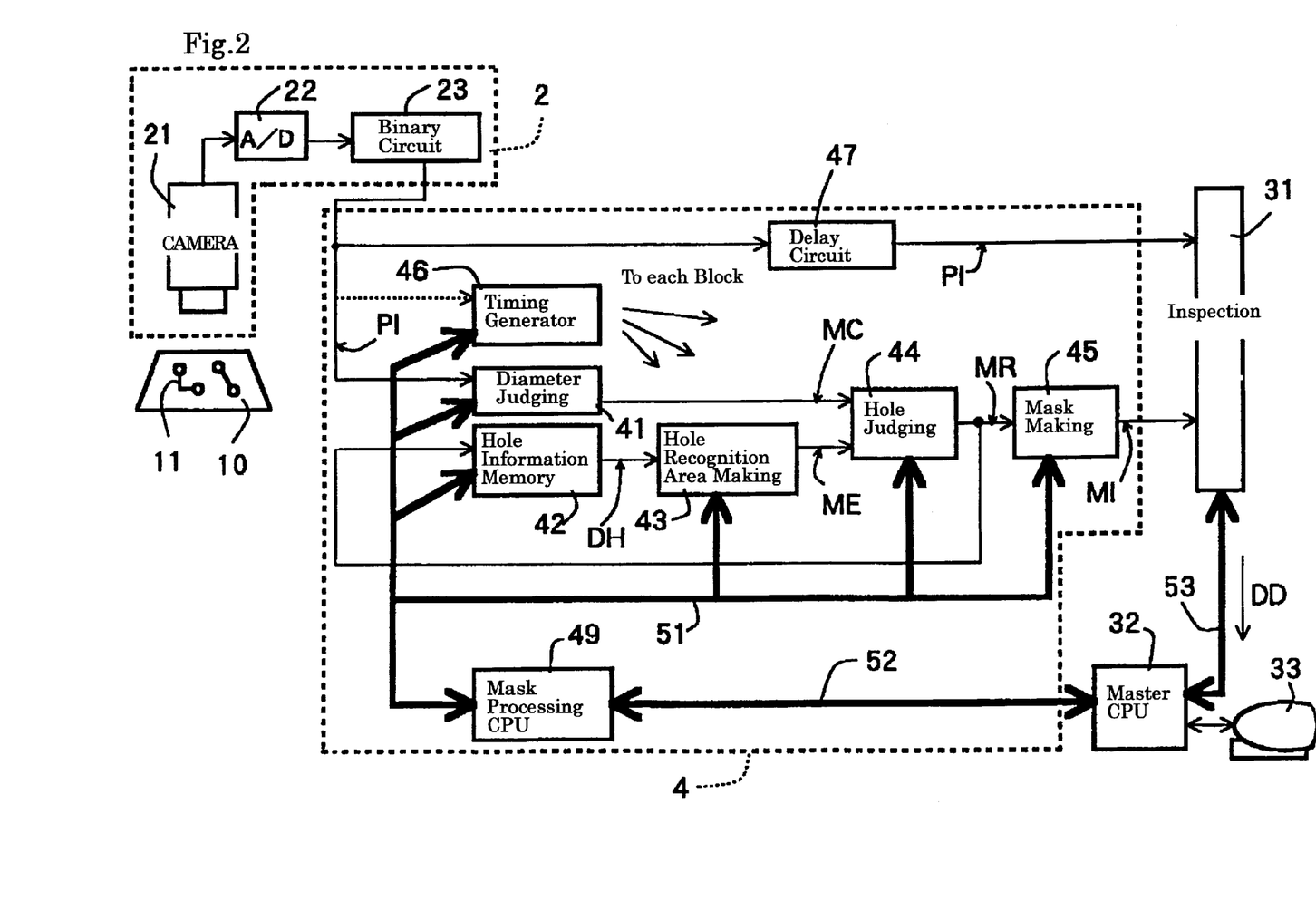
FIG. 2 is a block diagram of a wiring pattern inspecting apparatus according to an embodiment of the present invention.

At first, an imaging system 2 is described. The imaging system 2 has a function of capturing a pattern image from a wiring pattern 11 formed with a metal such as copper on a printed wiring board 10. Therefore the imaging system 2 comprises a CCD camera 21 to capture the wiring pattern 11, an A/D conversion unit 22 to convert an analog image to a digital signal and a binary circuit 23 to binarize the digital signal. That is, a pattern image PI output by the binary circuit 23 is a binary image made up of a black pixel and a white pixel. In the pattern image PI, a pixel of a place on the wiring pattern 11 is a white pixel generally, and a pixel of a place outside there is a black pixel. The place outside there is a part in a space part between patterns, a part in a via hole and a defect such as a pinhole.

Next, a mask processing unit 4 is described. The mask processing unit 4 has a function of making a mask image that shows an inspection outside area where the inspection is not done in the pattern image, and supplying the mask image in a inspection unit 31 with the pattern image. For this function, the mask processing unit 4 has following blocks: a diameter judging unit 41 that receives a pattern image PI from a binary circuit 23 of a imaging system 2, and then doing a diameter judgment of a part of a black pixel about each selected pixel in the pattern image PI; a hole information memory unit 42 that stores data of a via hole of a printed wiring board 10; a hole recognition area making unit 43 that makes a hole recognition effective signal ME based on data DH of the via hole; a hole judging unit 44 that compares the hole recognition effective signal ME with a judgment result MC of the diameter judging unit 41; a mask making unit 45 that makes a mask image MI based on the judgment result of the hole judging unit 44; a timing generator unit 46 that supplies a drive clock to each block; a mask processing CPU unit 49 that controls the mask processing unit 4 generally; and a delay circuit 47 that delays the pattern image PI during the time of making the mask image MI, and then supplies the pattern image PI to the inspection unit 31. Each these blocks are connected mutually by a local bus 51. And the mask processing CPU unit 49 is connected to the master CPU 32 by a communication bus 52.

Main structures among each blocks of a mask processing unit 4 are described roughly. At first a diameter judging unit 41 is a block doing a diameter judgment about a black pixel as described above. The diameter judgment is a process to get a pixel removed a pixel caused by a part between patterns from black pixels in the pattern image PI. The reason is because the part between patterns does not have to be masked because of a false signal being not caused. In addition, the reason is because the part can be definitely distinguished from a via hole with a point its covering long distance in consonance with a wiring pattern 11. A judgment result MC of the diameter judgment is sent to a hole-judging unit 44.

A hole information memory unit 42 is a block to store data DH of a via hole of a printed wiring board 10 as described before. A via hole often causes an origin of a false signal at a quality inspection of a printed wiring board 10, but a position of the via hole is determined every kind of a printed wiring board 10. To prepare the data of the position, for example, there is a method of using design data of the printed wiring board 10. Or there is a method of making from pattern image PIs about a standard board for the measurement. Although either method is preferable, in this embodiment, the method of using design data is adopted. In the case of using the standard board, a board formed only via holes by a specification same as the printed wiring board 10 may be used as the standard board. Or the first produced printed wiring board among a lot of printed wiring board 10 of a same kind produced by a same production lot may be used as the standard board. A data DH is sent to a hole recognition area making unit 43.

A hole recognition area making unit 43 is a block to make a hole recognition effective signal ME as described above. In this block, although the data DH supplied by the hole information memory unit 42 as it is may be used as the hole recognition effective signal ME, in this embodiment, the data DH expanded by a predetermined width (a number of pixel or magnification) is used as the hole recognition availability signal ME. The reason is because, in a printed wiring board 10, a real location of a via hole do not always corresponds with the data DH accurately, because of any dispersion by a machining accuracy. So, the expanding width may be put as a variableness depending on a grade of machining accuracy of the printed wiring board 10 (every kind has been decided). Therefore, the hole recognition effective signal ME covers all pixels in a region that there can be a via hole in the printed wiring board 10. If there is a black pixel as a mask candidate in the region, it is conceivable that the black pixel shows a real via hole. On the contrary, even if there is a black pixel as a mask candidate the region outside, a mask should not be generated in a standard with the black pixel because the black pixel is not related with a via hole of the printed wiring board 10. The hole recognition effective signal ME is sent to a hole judging unit 44.

A hole judging unit 44 is a block to compare a hole recognition effective signal ME with a judgment result MC of a diameter judging unit 41 as described above. The object of the hole judging unit 44 is to pick only a pixel truly caused by a via hole of a printed wiring board 10 from black pixels in a pattern image PI. For this, this block picks a black pixel authorized to a mask candidate based on the judgment result MC, and then compares the black pixel with the hole recognition effective signal ME. That is, a black pixel in a region of the recognized hole effective signal ME is judged as a signal truly caused by a via hole. On the other hand, a black pixel the region outside of the hole recognition effective signal ME is judged as a signal truly not caused by a via hole. A hole recognition signal MR of a pixel judged to be a black pixel truly caused by a via hole is sent to the mask making unit 45.

A mask making unit 45 is a block to make a mask image MI based on a judgment result of a hole judging unit 44 as described above. In this block basically, a mask image MI of one pixel is made of each pixel contained in a hole recognition signal MR sent by a hole judging unit 44. Therefore, a mask that just covers a via hole is provided. Afterwards, to depend on a required inspection precision, the mask may be expanded in magnification of a certain degree (such as 9 times) for each pixel contained the hole recognition signal MR. In that case, a little big (if it is 9 times, one pixel of width share is big) mask is provided. The mask image MI being made is sent to the inspection unit 31.

And next, an inspection unit 31 is described. The inspection unit 31 detects a shape that is to be finally a defect of a pattern from a pattern image PIs, and then outputs a detection signal DD toward a master CPU 32. For this, a mask image MI is input into an inspection unit 31, by the mask making unit 45, and the pattern image PI is input over a delay circuit 47 in order to match a timing with the input of the mask image MI. And, in the inspection unit 31, a defect shape of an open circuit, a short circuit, a conductor loss and so forth is extracted about a region outside of an inspection outside area selected by the mask image MI in the pattern image PI. For this, data of the defect shape may be pre-stored in the inspection unit 31, or may be supplied by the master CPU 32.

Next, actions of a quality inspection of a printed wiring board 10 by this wiring pattern inspecting apparatus are described. In this embodiment, data DH of a via hole, which is got from design data of the kind of a printed wiring board 10 as an inspected object is pre-stored in a hole information memory unit 42.

Figure 5:
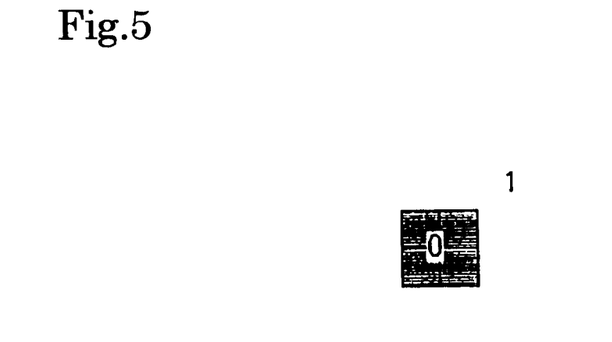
FIG. 5 is an explanatory drawing of a binary image of a pinhole.
Figure 6:
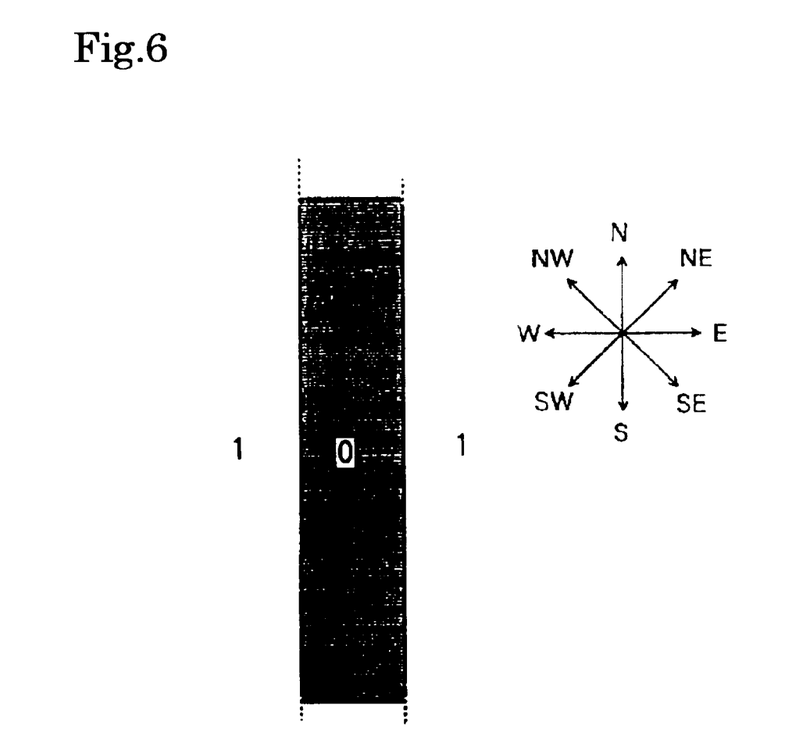
FIG. 6 is an explanatory drawing of a binary image of an insulation part between wiring patterns.

At first, a printed wiring board 10 to be inspected is put under a CCD camera 21, and a wiring pattern 11 on the printed wiring board 10 is captured. And an analog image is converted into a digital image with an A/D conversion unit 22, and then binarized with a binary circuit 23. Therefore, a pattern image PI of a binary image consisting of a black pixel and a white pixel is provided. The pattern image PI is sent to a mask processing unit 4, and input into a diameter judging unit 41. The pattern image PI contains a shape formed of a black pixel, such as a through hole (FIG. 3), a photo via hole (FIG. 4), a pinhole defect (FIG. 5) and a conductor spacing (FIG. 6). Of course, the photo via hole shown in FIG. 4 presents distorted shape by the reason explained in the background-art clause.

Figure 7:
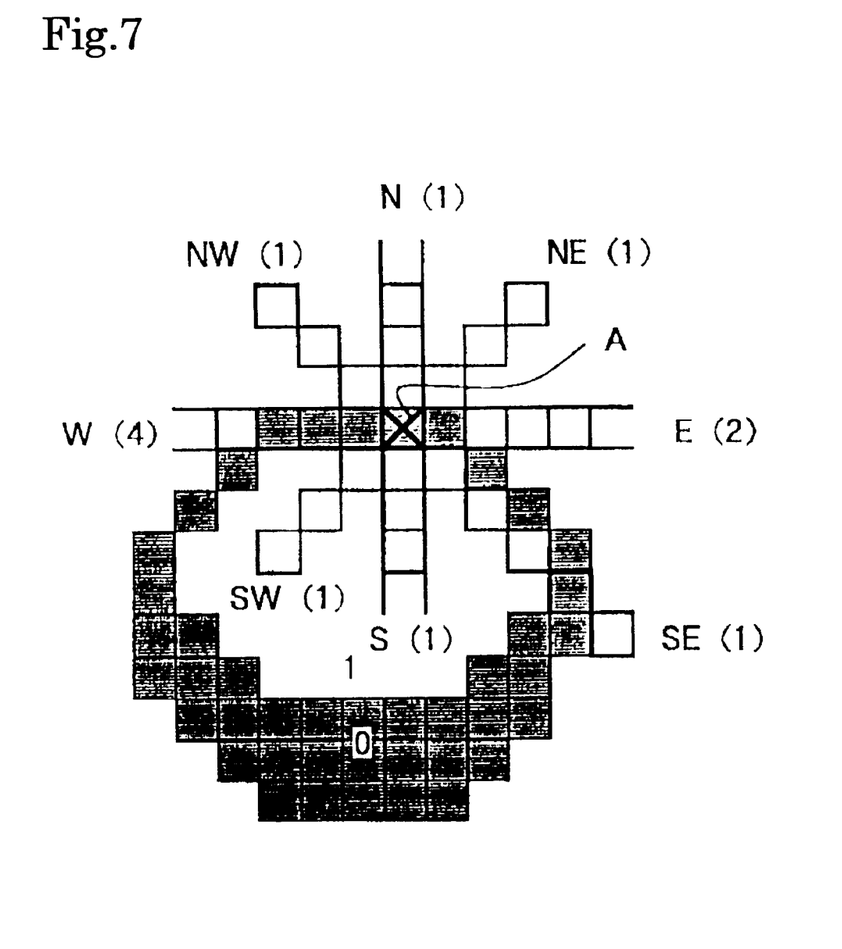
FIG. 7 is an explanatory drawing of a count of a black pixel on each direction of the wiring pattern inspecting apparatus according to the embodiment of the present invention.

In a diameter judging unit 41, the following works are done about a black pixel in a pattern image PI. That is, as shown in FIG. 7, a certain black pixel A is selected, and a number of a black pixel that continues from the selected black pixel A is counted on every direction of N, NE, E, SE, S, SW, W and NW direction of 8. The selected pixel A is counted as 1. As shown with a number in parenthesis on the right of an each direction sign in FIG. 7, the count value is "2" on the direction E, and the count value is "4" on the direction W. The count value of the direction aside from these is "1".

After a count value on each direction is prepared, the count value is compared with a number of pixel corresponding to a design value of a diameter of a through hole or a photo via hole contained by the printed wiring board 10 (in this embodiment, the diameter of the photo via hole is "11" pixels), and then judged whether OK or NG. For this comparison, a look-up table such as List I is prepared in a diameter judging unit 41. In a real look-up table, "count value" shown in List I is expressed with a binary number.

| List I | | | | | | | | |
|---|---|---|---|---|---|---|---|---|
| Count Value | 0 | 1 | 2 | ... | 10 | 11 | 12 | 13 | ... |
| Output Value | 0 | 1 | | | | | 0 | | |

That is, an output value "0" is assigned for a count value "0", "12" and more than "12", and an output value "1" is assigned for a count value of "1" ... "11". The output value "0" means that a count result of the direction is NG, and the output value "1" means that a count result is OK. And the number "11" of the greatest count that the output value "1" is assigned is a number of pixel corresponding to a design value of a diameter of a via hole. Therefore, in a case that a count value is an equilateral number of less than or equal to "11" that is a diameter of the via hole, the direction of the selected pixel is judged to be OK, and in a case aside the direction of the selected pixel is judged to be NG. Such a look-up table is prepared depending on each size of a via hole in a plural number class.

The fact that a judgment result becomes NG in the case of a count value "0" means a selected pixel cannot be authorized to a mask candidate in the case of the selected pixel being white. And, the fact that a judgment result becomes NG in the case of the count value being equal to or more than "12" means a selected pixel is not a pixel in a via hole because of a black pixel continues for a long distance. And in the case of a selected pixel A as shown in FIG. 7, every direction is judged to be OK. So similarly, in the case of a selected pixel being in a through hole (FIG. 3) or a pinhole defect (FIG. 5), every direction is judged to be OK. On the contrary of those, in the case of a selected pixel being in a conductor spacing (FIG. 6), the direction N and the direction S are judged to be NG.

Figure 8:
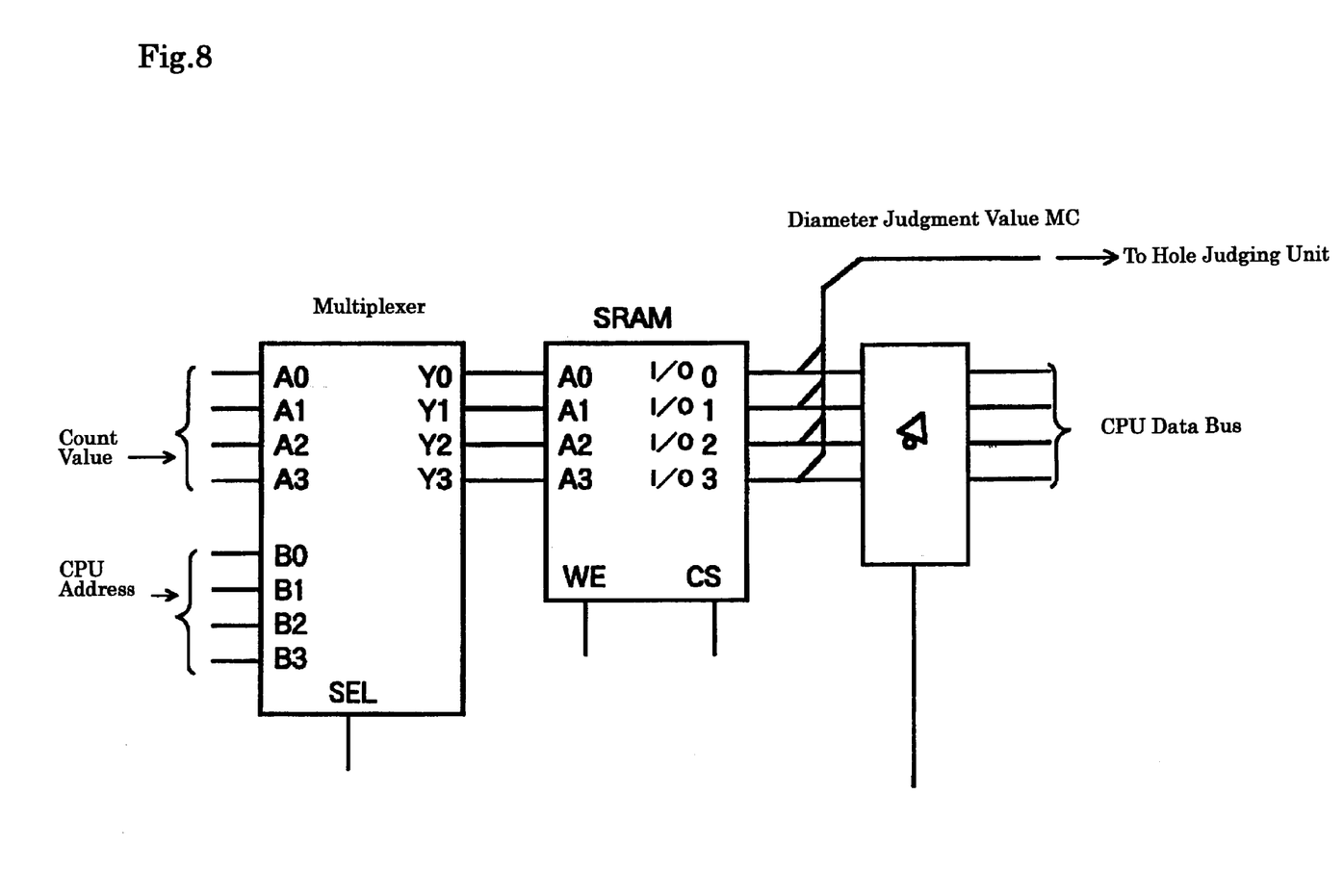
FIG. 8 is an explanatory drawing of a diameter judging process with a use of SRAM.

In a diameter judging unit 41, as shown in FIG. 8, a diameter judgment described above as a judgment about a direction is done with a SRAM. That is, in a system shown in FIG. 8, a count value is input into an address line of a SRAM (A0 ... A3) via a multiplexer, and then, depending on the count value, an output value (0 (NG) or 1 (OK) ) shown in the look-up table of List I is output into a data line of the SRAM (I/O 0 ... I/O 3). A total number of a direction shown in FIG. 7 is eight, so a circuit shown in FIG. 8 for the number of these directions is prepared, and then they performs parallel processing. In FIG. 8, the data line of the SRAM is 4 bits, so four ways of a judgment standard of OK or NG can be set. In this embodiment, only one way is set, but the 4 bits may be used as a look-up table judging four kinds of a hole diameter in simultaneously. An output value of each direction ("diameter judgment value MC" is said as follows) is sent to a hole judging unit 44. These processes are done about each pixel in a pattern image PI. In addition, to write the look-up table of List I into the SRAM shown in FIG. 8, a CPU data bus is connected to a CPU address, and then appointed data are input. The above is a processing in the diameter judging unit 41.

In parallel with a processing in above-mentioned diameter judging unit 41, a recognized hole effective signal ME is made in a hole information memory unit 42 and a hole recognition area making unit 43. For this, data DH with regard to a position and size of a via hole in a printed wiring board 10 to be inspected is extracted from design data beforehand, and then is prepared in the hole information memory unit 42. A value of the data DH is "1" about a pixel in a via hole, and a value is "0" about a pixel aside. 8 bits data width in the hole information memory unit 42 can be cope with maximum eight kinds of a via hole. And, in the hole recognition area making unit 43, the mask recognition effective signal ME may be made by expanding the data DH with a predetermined pixel width. The reason is because a position of a via hole can deviate in a predetermined clearance from a design value in a real printed wiring board 10. That is, the hole recognition effective signal ME is made with considering the greatest range that the via hole could deviate from the design value. The hole recognition effective signal ME is sent to a hole judging unit 44.

Next, a processing in a hole judging unit 44 is described. Into the hole-judging unit 44, a diameter judgment value MC of each direction on each black pixel in a pattern image PI is input into from the diameter judging unit 41, and a hole recognition effective signal ME is input from a hole recognition area making unit 43. Furthermore, a signal of an OK-continuing number is input from a mask processing CPU unit 49. The details on the OK-continuing number are explained later, but a value of it is fundamentally the same as a number of a direction used in the diameter judging unit 41, so in this embodiment, the value is "8". By these, a hole judgment is done about each black pixel in a pattern image PI with the hole judging unit 44.

Figure 9:
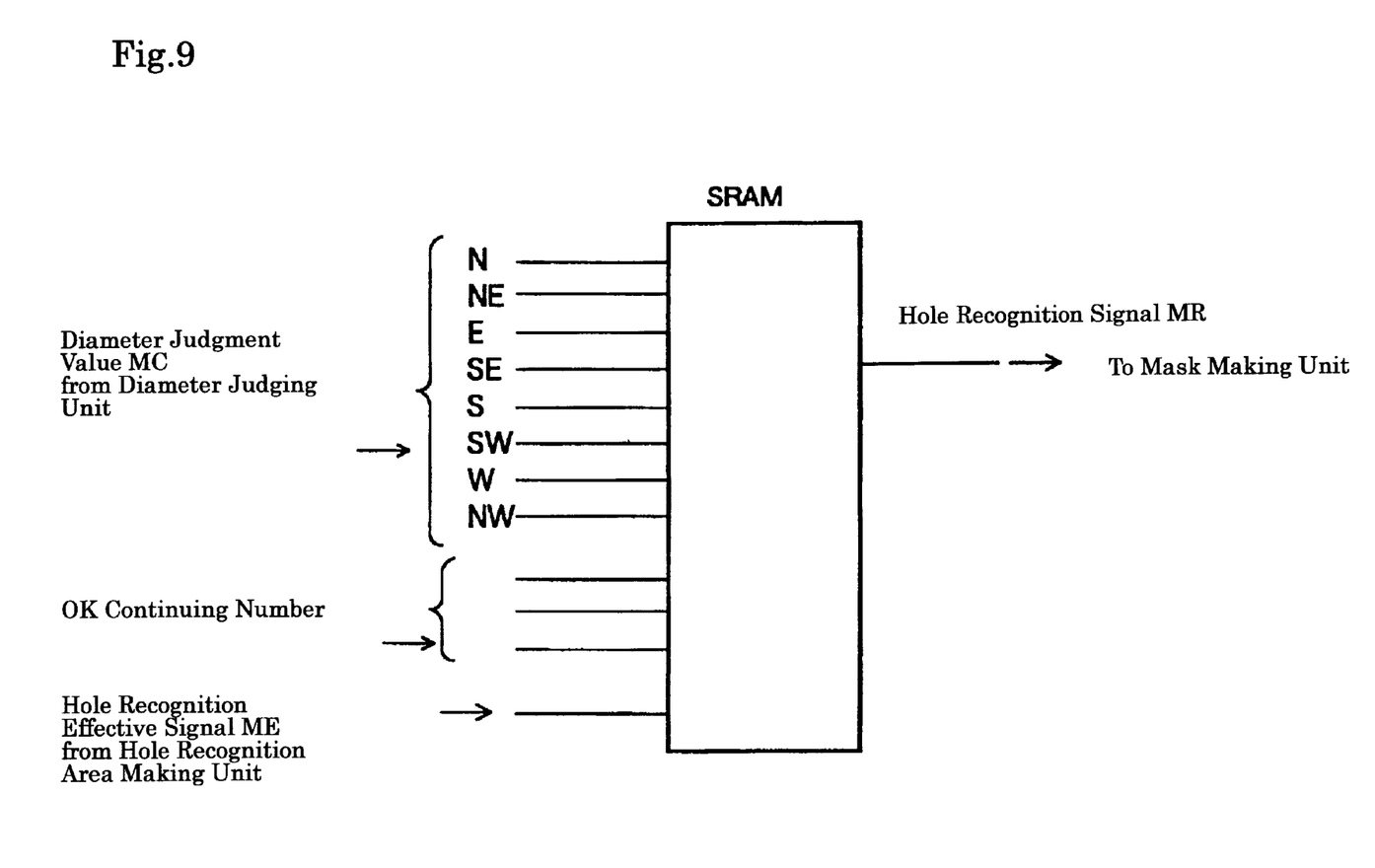
FIG. 9 is an explanatory drawing of a mask judging process with a use of SRAM.

This hole judgment is done with a SRAM as shown in FIG. 9. In a system shown in FIG. 9, a diameter judgment value MC of each direction on a black pixel in the pattern image PI is input into an address line of the SRAM. In addition, a signal of an OK-continuing number and a hole recognition effective signal ME are input, too. By these, a hole recognition signal MR is made as follows, and then output from a data line. At first, a number of a direction where a diameter judgment value MC is "1" namely OK in succession is counted. For example, on a selected pixel A shown in FIG. 7, the counted number becomes "8" because the diameter judgment is OK about all directions. Similarly, on a selected pixel in a through hole (FIG. 3) and a pinhole defect (FIG. 5), the counted number becomes "8". On the other hand, on a selected pixel in a conductor spacing (FIG. 6), the counted number becomes "3" because the direction where the diameter judgment is OK in succession is "NE, E, SE" and "SW, W, NW" by a reason of a judgment being NG about direction N and direction S.

And this counted number is compared with an OK-continuing number. In the case of the counted number being equal to or more than the OK-continuing number, a selected pixel is authorized to a mask candidate. And in the case of the counted number being less than the OK-continuing number, the selected pixel is not authorized to a mask candidate. For example, on a selected pixel A shown in FIG. 7, the counted number is "8", so the selected pixel is authorized to a mask candidate. Similarly, on a selected pixel in a through hole (FIG. 3) or a pinhole defect (FIG. 5), the selected pixel is authorized to a mask candidate. On the other hand, on a selected pixel in a conductor spacing (FIG. 6), the counted number is "3" and less than the OK-continuing number, so the selected pixel is not authorized to a mask candidate.

Figure 10:
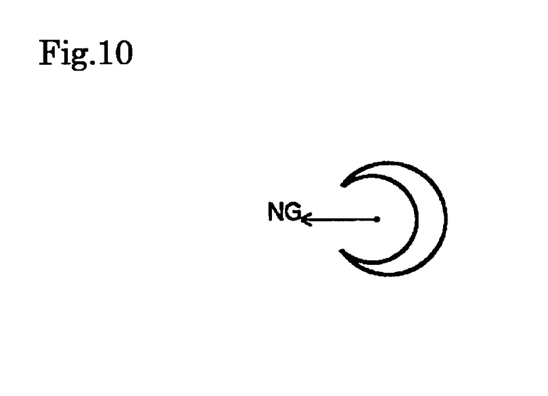
FIG. 10 is an explanatory drawing of a broken out in a land.

Still, the reason that an OK-continuing number sets into a total number of a direction is because a broken-out part in a land of a via hole circumference is not allowed in a normal printed wiring board 10. But there is a case that a some-extent broken-out part in a land is permitted by a specification of a printed wiring board 10 that may be formed with low grade forming accuracy. In that case as shown in FIG. 10, a land is broken in one place of somewhere, and then a diameter judgment on a direction that passes in the part becomes NG. It is unsuitable for a quality inspection that this selected pixel is not authorized to a mask candidate in this case. This can be avoided by setting a little small number than the total number of a direction into the OK-continuing number, or by fixing a result of the specific direction to "OK". Because of this, the OK-continuing number can be set changeably in a range of a total number of a direction, besides a result of a predetermined direction of a predetermined hole can be fixed.

After a selected pixel is authorized to a mask candidate, the selected pixel is sorted by a hole recognition effective signal ME. That is, only in the case that a selected pixel is recognized as a mask candidate, and besides, a position of the selected pixel is in a position range of the hole recognition effective signal ME, the selected pixel is judged to be a true hole recognition signal. By this sorting, a mask candidate pixel outside of the hole recognition effective signal ME is removed. The mask candidate pixel outside of the hole recognition effective signal ME is conceived a pixel not based on a via hole but based on a defect of pinholes. Therefore, a processing to mask such a pixel is unsuitable.

Authorization of a mask candidate and sorting by a hole recognition effective signal ME described above are done about each black pixel in a pattern image PI. Therefore, a hole recognition signal MR that is sent from a hole judging unit 44 to a mask making unit 45 is an information about a pixel finally sorted as a true standard of making a mask.

Then, in a mask making unit 45 that receives an input of a hole recognition signal MR makes a mask image MI. That is one pixel for each pixel contained by the hole recognition signal MR is made to be a mask pixel. Therefore, a mask image MI that just covers a via hole is provided (in FIG. 4, every pixel of "0", as it is, is made to be a mask) Still, a magnification of a certain degree (such as 9 times) may be submitted for each pixel contained by a hole recognition signal MR. Then, a little big (if it is 9 times, one pixel of width share is big) mask is provided (in a case of FIG. 4, a mask image expanded by one pixel for each pixel in a mask image that just covers the via hole is prepared). So, it may be said that the mask making unit 45 is an expanding filter to get an arbitrary mask size. A mask image MI expresses a part considered to be targets outside of a quality inspection in a pattern image PI.

After a mask image MI is made, an inspection processing is done with an inspection unit 31. For this, a mask image MI and a pattern image PI are input into this inspection unit 31. At this time, the pattern image PI input into inspection unit 31 receives a delay processing for a mask processing time share by a delay circuit 47 to be aligned with the mask image MI. In addition, in the inspection unit 31, data of a defect shapes such as an open circuit, a short circuit and a conductor loss is supplied beforehand by a master CPU 32. Therefore, in the inspection unit 31, a defect shape or a shape to resemble a defect shape can be extracted from a region outside of the mask image MI in the pattern image PI. A data DD such as a defect shape being extracted is sent to the master CPU 32, and then totalized. Here, on some specification of a printed wiring board 10, there is a case that a shape to resemble the defect shape is contained in a good wiring pattern. In such a case, it is preferable to prepare a data to exclude the shape from an inspection subject beforehand in the inspection unit 31. Defect data totalized by the master CPU 32 may be displayed through a terminal 33, or may be output.

As described above, a printed wiring board 10 is inspected. Then, even if another printed wiring board 10 of the same kind and belonged to the same production lot is inspected subsequently, same as the first piece, a hole recognition signal MR is extracted from a pattern image PI of the printed wiring board 10, and then a mask image MI is made again. The reason is because a quality inspection is must be done with a highly precise mask image MI matched in a hole shape of the printed wiring board 10.

As discussed in detail above, in a printed wiring board inspection apparatus of this preferred embodiment, about each black pixel in a pattern image PI formed of binary data gotten by capturing a printed wiring board 10, with a diameter judging unit 41, a number of a black pixel that continues from a selected pixel is counted on every eight direction, and then a diameter judgment value MC is output. Here, even one pixel of a black pixel can is extracted without being overlooked, because a count value of the selected pixel can be counted as "1" on every direction. Because of this, even if the pattern image PI includes a black pixel group of a distorted shape such as a via hole, a hole recognition signal MR is made without a leak of one pixel. Of course, a through hole extraction by a radius standard judgment of the conventional technique can be used. So, an appropriate mask that just covers a hole shape can be made in a mask making unit 45 even if the printed wiring board 10 includes a photo via hole. Therefore, a wiring pattern inspecting apparatus that is hard to occur of a leak inspection while eliminating an occurrence of a false signal caused by a via hole is realized.

In addition, in this embodiment, in a hole judging unit 44, a value of an OK-continuing number is used as a judgment standard to extract a hole recognition signal MR based on a diameter judgment value MC and a hole recognition effective signal ME. And the value of the OK-continuing number is a variableness that can be set a value in a range of a total number of the direction. Therefore, even if by a specification, a printed wiring board 10 is permitted to includes a broken-out part of a certain degree in a land because of its low grade of machining accuracy, an inspection that is hard to occur of a leak while eliminating an occurrence of a false signal is realized because the inspection can be done with a reasonable mask image in proportion to the specification.

By the way, an embodiment of the present invention is not limited to the preferred embodiment described above, and it is apparent that numerous improvements and modifications can be made thereto with the scope not departing from the concept of the invention. For example, the present invention can be made as following. By a diameter judgment of a pattern image PI based on a hole recognition effective signal ME, a mask image may be made at higher speed. And, binary data are not limited to, and even data that is equal to or more than ternary can be used. And, a number of a direction of a diameter judgment in a diameter judging unit 41 is not limited to "8". For example, "4", "12", "16" and so on are thought about, and it does not need to be a multiple of 4.

In addition, instead of using a design data of a printed wiring board 10, a data DH about a via hole, which is supplied from a hole information memory unit 42 to a hole recognition area making unit 43 may be prepared by another means. For example, a pattern image PI is made about a standard board formed same holes as a printed wiring board 10 to be inspected, and in processing of a hole judging unit 44 on the pattern image PI (FIG. 9), a hole recognition signal MR is made without using of a hole recognition effective signal ME, with only using a diameter judgment value MC and an OK-continuing number, and then a hole recognition signal MR fed back to a hole information memory unit 42 may be made to be a data DH. In that case, furthermore, by feeding back the hole recognition signal MR to the hole information memory unit 42, whenever a printed wiring board 10 is inspected, a learning effect is given to that apparatus.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An image processor comprising:
    a pattern image making unit configured to make a pattern image formed from pixel data obtained by capturing a surface of an object to be inspected, said pattern image including black pixels;
    a mask candidate pixel determining unit configured to determine whether each black pixel of said black pixels included in said pattern image is a mask candidate pixel, said mask candidate pixel determining unit comprising:
        a selecting unit configured to select one black pixel from said black pixels included in said pattern image;
        a counter configured to count in each of plural directions a pixel number of consecutive black pixels which consecutively continue from said selected one black pixel along said each of plural directions;
        a comparison unit configured to determine with respect to said each of plural directions an OK direction along which the pixel number is at most a predetermined reference pixel number;
        a determining unit configured to determine that the selected one black pixel is the mask candidate pixel when a direction number of said OK direction with respect to the selected one black pixel is at least a predetermined reference direction number;
    a general mask area storage unit configured to memorize a general mask area in which an inspection on the surface of the object is not generally performed; and
    a mask area determining unit configured to determine a mask area in which the inspection is not performed based on the mask candidate pixel and the general mask area.

2. An image processor according to claim 1, wherein said predetermined reference pixel number is determined based on a size of a part on the surface of the object, the inspection being not performed on the part.

3. An image processor according to claim 1, wherein said predetermined reference direction number is variable.

4. An image processor according to claim 1, wherein said predetermined reference direction number is equal to a number of said plural directions.

5. An image processor according to claim 1, wherein said general mask area is determined based on a design of a wiring pattern provided on the surface of the object.

6. An image processor according to claim 1, wherein the mask area includes a via hole.

7. An image processor comprising:
    pattern image making means for making a pattern image formed from pixel data obtained by capturing a surface of an object to be inspected, said pattern image including black pixels;
    mask candidate pixel determining means for determining whether each black pixel of said black pixels included in said pattern image is a mask candidate pixel, said mask candidate pixel determining means comprising:
        selecting means for selecting one black pixel from said black pixels included in said pattern image;
        counter means for counting in each of plural directions a pixel number of consecutive black pixels which consecutively continue from said selected one black pixel along said each of plural directions;
        comparison means for determining with respect to said each of plural directions an OK direction along which the pixel number is at most a predetermined reference pixel number;
        determining means for determining that the selected one black pixel is the mask candidate pixel when a direction number of said OK direction with respect to the selected one black pixel is at least a predetermined reference direction number;
    general mask area storage means for memorizing a general mask area in which an inspection on the surface of the object is not generally performed; and
    mask area determining means for determining a mask area in which the inspection is not performed based on the mask candidate pixel and the general mask area.

8. An image processor according to claim 7, wherein said predetermined reference pixel number is determined based on a size of a part on the surface of the object, the inspection being not performed on the part.

9. An image processor according to claim 7, wherein said predetermined reference direction number is variable.

10. An image processor according to claim 7, wherein said predetermined reference direction number is equal to a number of said plural directions.

11. An image processor according to claim 7, wherein said general mask area is determined based on a design of a wiring pattern provided on the surface of the object.

12. An image processor according to claim 7, wherein the mask area includes a via hole.

13. An image processing method comprising:
    making a pattern image formed from pixel data obtained by capturing a surface of an object to be inspected, said pattern image including black pixels;
    determining whether each black pixel of said black pixels included in said pattern image is a mask candidate pixel, said mask candidate pixel determining means comprising:
        selecting one black pixel from said black pixels included in said pattern image;

counting in each of plural directions a pixel number of consecutive black pixels which consecutively continue from said selected one black pixel along said each of plural directions;

determining with respect to said each of plural directions an OK direction along which the pixel number is at most a predetermined reference pixel number;

determining that the selected one black pixel is the mask candidate pixel when a direction number of said OK direction with respect to the selected one black pixel is at least a predetermined reference direction number;

memorizing a general mask area in which an inspection on the surface of the object is not generally performed; and determining means for determining a mask area in which the inspection is not performed based on the mask candidate pixel and the general mask area.

14. An inspection apparatus comprising:

a pattern image making unit configured to make a pattern image formed from pixel data obtained by capturing a surface of an object to be inspected, said pattern image including black pixels;

a mask candidate pixel determining unit configured to determine whether each black pixel of said black pixels included in said pattern image is a mask candidate pixel, said mask candidate pixel determining unit comprising:

a selecting unit configured to select one black pixel from said black pixels included in said pattern image;

a counter configured to count in each of plural directions a pixel number of consecutive black pixels which consecutively continue from said selected one black pixel along said each of plural directions;

a comparison unit configured to determine with respect to said each of plural directions an OK direction along which the pixel number is at most a predetermined reference pixel number;

a determining unit configured to determine that the selected one black pixel is the mask candidate pixel when a direction number of said OK direction with respect to the selected one black pixel is at least a predetermined reference direction number;

a general mask area storage unit configured to memorize a general mask area in which an inspection on the surface of the object is not generally performed;

a mask area determining unit configured to determine a mask area in which the inspection is not performed based on the mask candidate pixel and the general mask area; and an inspecting unit configured to detect a defect shape from the pattern image except for the mask area.

15. An inspection apparatus according to claim 14, wherein said predetermined reference pixel number is determined based on a size of a part on the surface of the object, the inspection being not performed on the part.

16. An inspection apparatus according to claim 14, wherein said predetermined reference direction number is variable.

17. An inspection apparatus according to claim 14, wherein said predetermined reference direction number is equal to a number of said plural directions.

18. An inspection apparatus according to claim 14, wherein said general mask area is determined based on a design of a wiring pattern provided on the surface of the object.

19. An inspection apparatus according to claim 14, wherein the mask area includes a via hole.

* * * * *